US008733641B1

(12) United States Patent
Drew et al.

(10) Patent No.: US 8,733,641 B1
(45) Date of Patent: May 27, 2014

(54) ELECTRONIC KIOSK SYSTEM AND METHOD FOR DISPENSING MEDICAL SMART CARDS AND MANAGING HEALTHCARE INFORMATION AND SERVICES

(75) Inventors: Norman J. Drew, Lakeland, FL (US); James Owen Childers, Freeland, WA (US); Jeff Lee, Lake Worth, FL (US)

(73) Assignee: Digital Processing Systems, LLC., Lakeland, FL (US)

( * ) Notice: Subject to any disclaimer, the term of this patent is extended or adjusted under 35 U.S.C. 154(b) by 38 days.

(21) Appl. No.: 13/493,109

(22) Filed: Jun. 11, 2012

Related U.S. Application Data

(60) Provisional application No. 61/496,654, filed on Jun. 14, 2011.

(51) Int. Cl.
*G06Q 50/00* (2012.01)
(52) U.S. Cl.
USPC .............................................. 235/381; 705/2
(58) Field of Classification Search
USPC ....................................... 235/381, 382; 705/2
See application file for complete search history.

(56) References Cited

U.S. PATENT DOCUMENTS

| | | | |
|---|---|---|---|
| 4,093,315 A | 6/1978 | Page et al. | |
| 4,099,644 A | 7/1978 | Nuttall et al. | |
| 4,179,165 A | 12/1979 | Page et al. | |
| 4,410,100 A | 10/1983 | Simmons et al. | |
| 4,423,909 A | 1/1984 | Page et al. | |
| 4,449,113 A | 5/1984 | Gould et al. | |
| 4,478,617 A | 10/1984 | Rees | |
| 4,719,338 A | 1/1988 | Avery et al. | |
| 5,059,536 A | 10/1991 | Page et al. | |
| 5,096,819 A | 3/1992 | Page et al. | |
| 5,324,472 A | 6/1994 | Page et al. | |
| 5,434,395 A | 7/1995 | Storck et al. | |
| 5,453,813 A | 9/1995 | Arnold et al. | |
| 5,515,137 A | 5/1996 | Arnold et al. | |
| 5,728,998 A | 3/1998 | Novis et al. | |
| 5,763,862 A | 6/1998 | Jachimowicz et al. | |
| 5,821,516 A | 10/1998 | Vandenengel | |
| 5,867,795 A | 2/1999 | Novis et al. | |
| 5,949,047 A | 9/1999 | Abe et al. | |
| 6,089,459 A | 7/2000 | Eisele et al. | |
| 6,155,233 A | 12/2000 | Wade et al. | |
| 6,257,486 B1 | 7/2001 | Teicher et al. | |
| 6,422,394 B1 | 7/2002 | Page | |
| D482,451 S | 11/2003 | Page et al. | |
| 6,688,853 B1 | 2/2004 | Burkett et al. | |
| 6,715,679 B1 | 4/2004 | Infosino | |
| 6,800,810 B1 | 10/2004 | Page | |
| 6,914,786 B1 | 7/2005 | Paulsen et al. | |
| 7,359,489 B2 | 4/2008 | Page et al. | |
| 7,562,815 B2 | 7/2009 | Page | |
| 7,583,621 B2 | 9/2009 | Qi et al. | |

(Continued)

*Primary Examiner* — Daniel Hess
(74) *Attorney, Agent, or Firm* — H. John Rizvi; Gold & Rizvi, P.A.

(57) ABSTRACT

The present invention provides an electronic kiosk for dispensing medical smart cards and healthcare related forms, and for managing individual healthcare services and information. The electronic kiosk provides access control to healthcare information stored on medical smart cards by including biometric authentication, a high definition camera for capturing images, and an interactive touch screen. A central client-server configuration is provided where a plurality of electronic kiosks are connected to an application server, via a network. Individuals may access the electronic kiosk to request prescription refills and receive confirmation via, text or email when the prescription is ready.

16 Claims, 4 Drawing Sheets

(56) References Cited

U.S. PATENT DOCUMENTS

| | | |
|---|---|---|
| 7,613,481 B2 | 11/2009 | Aubert |
| 7,724,137 B2 | 5/2010 | Page |
| 7,734,036 B1 | 6/2010 | Page et al. |
| 8,212,675 B2 | 7/2012 | Page |
| 8,397,988 B1 | 3/2013 | Zuili |
| 2002/0144936 A1 | 10/2002 | Page |
| 2004/0050733 A1 | 3/2004 | Page et al. |
| 2004/0232219 A1 | 11/2004 | Fowler |
| 2005/0099766 A1 | 5/2005 | Fraley et al. |
| 2005/0212657 A1 | 9/2005 | Simon |
| 2006/0052120 A1 | 3/2006 | Kodim et al. |
| 2006/0072484 A1 | 4/2006 | Qi et al. |
| 2006/0098807 A1 | 5/2006 | Page et al. |
| 2006/0106646 A1 | 5/2006 | Squilla et al. |
| 2006/0143052 A1 | 6/2006 | Fotsch et al. |
| 2006/0176524 A1 | 8/2006 | Willrich |
| 2006/0249576 A1 | 11/2006 | Nakada et al. |
| 2007/0108267 A1* | 5/2007 | Jonsson et al. ............... 235/379 |
| 2007/0145121 A1 | 6/2007 | Dallal et al. |
| 2007/0194911 A1 | 8/2007 | Page |
| 2007/0210161 A1 | 9/2007 | Page |
| 2007/0278294 A1 | 12/2007 | Page |
| 2008/0067237 A1* | 3/2008 | Barcelou ....................... 235/379 |
| 2008/0203157 A1* | 8/2008 | Thorsen et al. ............... 235/382 |
| 2009/0039150 A1 | 2/2009 | Lay |
| 2009/0166375 A1 | 7/2009 | Butler et al. |
| 2009/0250515 A1 | 10/2009 | Todd et al. |
| 2009/0272800 A1 | 11/2009 | Page |
| 2010/0017296 A1* | 1/2010 | Spignesi et al. ............ 705/14.66 |
| 2010/0214100 A1 | 8/2010 | Page |
| 2011/0037542 A1 | 2/2011 | Page et al. |
| 2011/0055155 A1 | 3/2011 | Page et al. |
| 2011/0071949 A1 | 3/2011 | Petrov et al. |
| 2011/0208574 A1* | 8/2011 | Hinojosa et al. ........... 705/14.23 |
| 2012/0011565 A1 | 1/2012 | Garlie et al. |
| 2013/0144792 A1 | 6/2013 | Nilsson et al. |
| 2013/0173475 A1 | 7/2013 | Lund |

* cited by examiner

ELECTRONIC KIOSK SYSTEM AND METHOD FOR DISPENSING MEDICAL SMART CARDS AND MANAGING HEALTHCARE INFORMATION AND SERVICES

CROSS-REFERENCE TO RELATED APPLICATION

This application claims the benefit of U.S. Provisional Patent Application Ser. No. 61/496,654 filed Jun. 14, 2011, which is incorporated herein in its entirety.

FIELD OF THE INVENTION

The present disclosure relates generally to electronic kiosks. More particularly, the present disclosure relates to an electronic kiosk system and method for dispensing medical smart cards, and for managing individual healthcare services and information. The electronic kiosk provides access control to healthcare information stored on medical smart cards by including biometric authentication, a high definition camera for capturing images, and a large interactive touch screen. A central client-server configuration is provided where a plurality of electronic kiosks are connected to an application server, via a network. Individuals may access an electronic kiosk to request prescription refills and receive confirmation via, text or email when the prescription is ready.

BACKGROUND OF THE INVENTION

Electronic or interactive kiosks are generally exhibits that typically include a computer system that is configured to provide access to applications and information for a variety of different uses. The computer system is securely housed within the electronic kiosk and generally includes software for providing application programming, and hardware that includes an electronic display and a plurality of keys for inputting data and navigating through application programs. Most electronic kiosks are located in high traffic settings where individuals congregate such as in banks, hotels, airports, malls, universities and department stores, to name a few.

Electronic kiosks come in all shapes and sizes. For example, some kiosks are designed to fit securely within walls of buildings while others are mobile for transporting the kiosks from one location to another. The structural framework of most kiosks consists generally of plastic, wood, metal, or any combination thereof. Floor kiosks provide a popular style of electronic kiosk that includes a structural housing defined by sidewalls, a back panel, a front panel and a top member. A computer system is safely stored within the housing of the kiosk, and an electronic display screen and input keys are disposed in a central region of the kiosk to provide easy, accessible use.

Electronic kiosks find use in diverse applications. For example, electronic kiosks are often used for entertainment or educational purposes. Such kiosks allow individuals to interact with application programs for viewing movies, determining times and dates of shows, concerts or events, accessing bulletin boards, reviewing classifications, or learning about possible seminars, programs or classes. Electronic kiosks also play a vital role in commerce. Such kiosks often include card readers that are designed to interface with credit cards, bank cards, and charge cards. Electronic kiosks can be used to make purchases, pay bills, or transact business. Electronic kiosks are also used in banking to allow individuals to manage banking accounts, withdraw funds, and apply for credit.

Few electronic kiosks have been designed for use in the medical industry. Most kiosks include computer systems that allow professionals to access medical information pertaining to scholarly teachings, medical procedures, medical product information, government warnings, studies, and information relating to medication. Alternative forms of kiosks have been designed to interface with information storage cards. For example, cards including bar codes or magnetic stripe cards are often used to store individual medical information. Kiosks are adapted to include magnetic head readers and bar code readers to read information stored on such cards. One drawback however of such systems is that the bar code card and magnetic stripe card provide poor security and thus compromise a patient's privacy and security of information. To address the security drawbacks of the prior art cards, smart cards have been developed to enhance security access to information stored on the smart card, and to store more information on the smart card.

With advancement in storage information technology, electronic kiosks have been adapted for use with smart cards to read information stored thereon. Such kiosks typically include a card reader slot adapted to receive a smart card therein, and a card reader that interfaces with the smart card to read medical information stored on the smart card. Input keys and an electronic display are used navigate through information and data, and view stored information.

Although prior art kiosk systems are designed for use with smart cards to view information stored on the smart cards, conventional kiosk systems suffer from certain drawbacks. For example, conventional kiosk systems are not tailored for dispensing medical smart cards. Traditional kiosks allow individuals to view information on cards but do not provide immediate access to a smart card for managing healthcare information. An individual may wish to have a medical smart card that includes up-to-date medical information which can be used at hospitals, clinics, and emergency rooms that have compatible card readers. Most critical emergency situations make it difficult for both patients and medical personnel to effectively communicate with each other. For example, an individual may suffer from a heart attack, a stroke, or experience a severe allergic reaction. The trauma and adverse effects imposed on an individual often makes it difficult for the patient to relay important, vital medical information to the attending physician or nurse or to consent to medical treatment. As a result, the lack of vital information can compromise a patient's treatment. The patient may be confused, unconscious, or physically impaired making it difficult or impossible for the patient to remember or relay health-related information. Thus, an individual may wish to have a smart card to provide vital life-saving information to medical service providers in the event of an emergency where a cardholder is unable to effectively communicate with medical personnel. Also, conventional kiosk systems do not include a kiosk that permits individuals to fully manage medical healthcare services such as making appointments, acquiring medical directive forms, or requesting prescription refills and receiving confirmation.

What is desired is an electronic kiosk system and method for dispensing medical smart cards, and managing healthcare information and services. The medical smart card is used to store medical information and to provide vital life-saving information to medical service providers in the event of an emergency. What is also desired is an electronic kiosk system that includes an electronic kiosk which provides secure, access control by including biometric authentication, provides a variety of medical directive forms, and is accessible to request prescription refills and receive confirmation.

SUMMARY OF THE INVENTION

A first aspect of the present invention provides, a card dispensing kiosk comprising: a frame including a base joined to two vertical sidewalls extending upwards from the base, a central panel, a front panel, a rear panel, and a lateral shelf, all assembled together to form a chamber for housing a computer system for operating electronic components including: an interactive touch screen accessible through an opening formed in the central panel; a first printer for printing receipts, and a second printer for printing healthcare related forms where the first printer is associated with a printer slot provided in the central panel, and where the second printer us associated with a second printer slot provided in the front panel; a card reader system selectively interfacing with medical smart cards including healthcare information stored thereon, and credit cards; a card dispenser associated with a card dispensing slot provided in the central panel where the card dispenser is adapted to sequentially dispense medical smart cards upon each successful completion of an application process; a biometric authentication system including a biometric sensor situated on the central panel; a high definition camera operated to capture images of individuals using the kiosk, and a keyboard disposed on or within the lateral shelf, wherein the central panel is setback a distance from front longitudinal edges of the vertical sidewalls to provide a zone of privacy.

A second aspect of the card dispensing kiosk provides a computer system including a processor, memory, an internal hard drive, a trackball mounted near the keyboard, and software including medical application software and programs.

In another aspect, the card dispensing kiosk further includes an audio system electrically coupled to the computer system and including one or more speakers associated with speaker holes formed in the central panel. A ventilation system is also included for circulating air out from and within the kiosk.

In yet another aspect, the card dispensing kiosk further includes wireless technology including any one of 2G, 3G, 4G, 5G, Wi-Fi, WiMax or Blue Tooth technology, a secure Global System for Mobile Communication (GSM) connection, and a GSM modem. A handicapped audio access port provided is provided on the central panel where the audio access port electrically coupled to the computer system for providing audible information.

In another aspect, the card dispenser includes a card ejector for ejecting smart cards, and a card storage bin for storing a plurality of smart cards therein. The card dispensing kiosk further includes an input/output (I/O) interface including any of a telephone modem, a cable modem, a GSM modem, universal serial bus (USB) and/or Ethernet ports, parallel or serial connectors, and HDMI connections.

In yet another aspect, the biometric sensor includes any one of a fingerprint sensor, a palm sensor, a speech recognition system, or a retinal validation sensor. The biometric authentication system further includes a biometric signature database including biometric signatures associated with a plurality of individuals authorized to use the card dispensing kiosk. The healthcare information includes an individual's demographic and profile information, medical emergency contact information, physician/specialist information, medical conditions, procedural medical history, information relating to prescription and over-the-counter medicine, vitamins or supplements, vaccination or immunization historical records, advance directives, medical insurance information, and a photograph of an individual owner of said medical smart card, and wherein said healthcare related forms includes any of service agreements, authorizations to treat, advanced directives, immunization forms, privacy statements, laws and rules, power of attorney, and living will.

In yet another aspect of the present invention there is provided, a method of managing healthcare information and services comprising: providing an electronic kiosk comprising: a frame including a base joined to two vertical sidewalls extending upwards from the base, a central panel, a front panel, a rear panel, and a lateral shelf, all assembled together to form a chamber for housing a computer system including a processor, and memory, and kiosk system components, where the computer system is electrically connected to and operating the kiosk system components. The kiosk system components include: an interactive touch screen; a first printer for printing receipts, and a second printer for printing healthcare related forms, where the printers are associated with slots provided in the central panel; a card reader system selectively interfacing with medical smart cards including healthcare information stored thereon, and credit cards; a card dispenser associated with a card dispensing slot provided in the central panel; a biometric authentication system including a biometric sensor situated on the central panel; a high definition camera operated to capture images of individuals using the kiosk, and an audio system including speakers and a handicapped audio access port. The method includes the step of operating an application server hosting medical service application software associated with managing individual healthcare information and services, where the electronic kiosk electrically communicates with the application server over a wired or wireless network; capturing an image with the high definition camera of an individual using the kiosk, and processing a biometric signature of an individual user, providing information of an individual user to apply for a medical smart card, and sequentially dispensing a medical smart card upon successful completion of each application process completed by individual users, or selectively interfacing a medical smart card with the card reader system of the kiosk to view and manage healthcare information and services when the biometric signature of the individual user is authenticated, where the healthcare information stored on the smart card.

In another aspect, the method includes the step of requesting prescription refills of medication and sending a text or email message confirming readiness of the refills. Processing a biometric signature of an individual user includes the step of reading a biometric fingerprint signature of the user when the user places a finger on the biometric sensor. The step of providing information of an individual user to apply for a medical smart card includes the step of entering personal information, and paying a fee with a credit card to complete the application process.

In yet another aspect, the method includes a step of printing a receipt via, the first printer, and further including the step of printing healthcare related forms via, the second printer where the receipt and healthcare related forms are forwarded through a corresponding slot. The medical service application software provides an interface on the touch screen including menus, links, tabs and icons for managing individual healthcare information and services, where the medical service application software is executed on the electronic kiosk.

In another aspect, the present invention provides, an electronic kiosk for dispensing and interfacing with medical smart cards, the electronic kiosk comprising a computer system having memory and a processor and including: an interactive touch screen; a first printer for printing receipts, and a second printer for printing healthcare related forms; a card reader system selectively interfacing with medical smart cards including healthcare information stored on the medical smart card, and credit cards; a card dispenser sequentially dispensing medical smart cards upon each successful completion of an application process and payment of a fee; a biometric authentication system including a biometric fingerprint sensor; a high definition camera operated to capture images of individuals using the kiosk, input devices for inputting data, and a machine readable medium including a medical service application software stored thereon that when executed on the computer system displays an interface on the interactive touch screen, where the interface provides menus, links, tabs, and icons, associated with managing healthcare information, and allowing a user to selectively read healthcare information stored on the medical smart card, or to selectively write healthcare information to the medical smart card when the medical smart card electrically communicates with the card reader system and when the biometric authenticating system correctly authenticates a fingerprint signature of an authorized user.

These and other advantages of the invention will be further understood and appreciated by those skilled in the art by reference to the following written specifications, claims, and appended drawings.

BRIEF DESCRIPTION OF THE DRAWINGS

The invention will now be described, by way of example, with reference to the accompanying drawings, in which.

Like reference numerals refer to like parts throughout the various views of the drawings.

DETAILED DESCRIPTION OF THE INVENTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
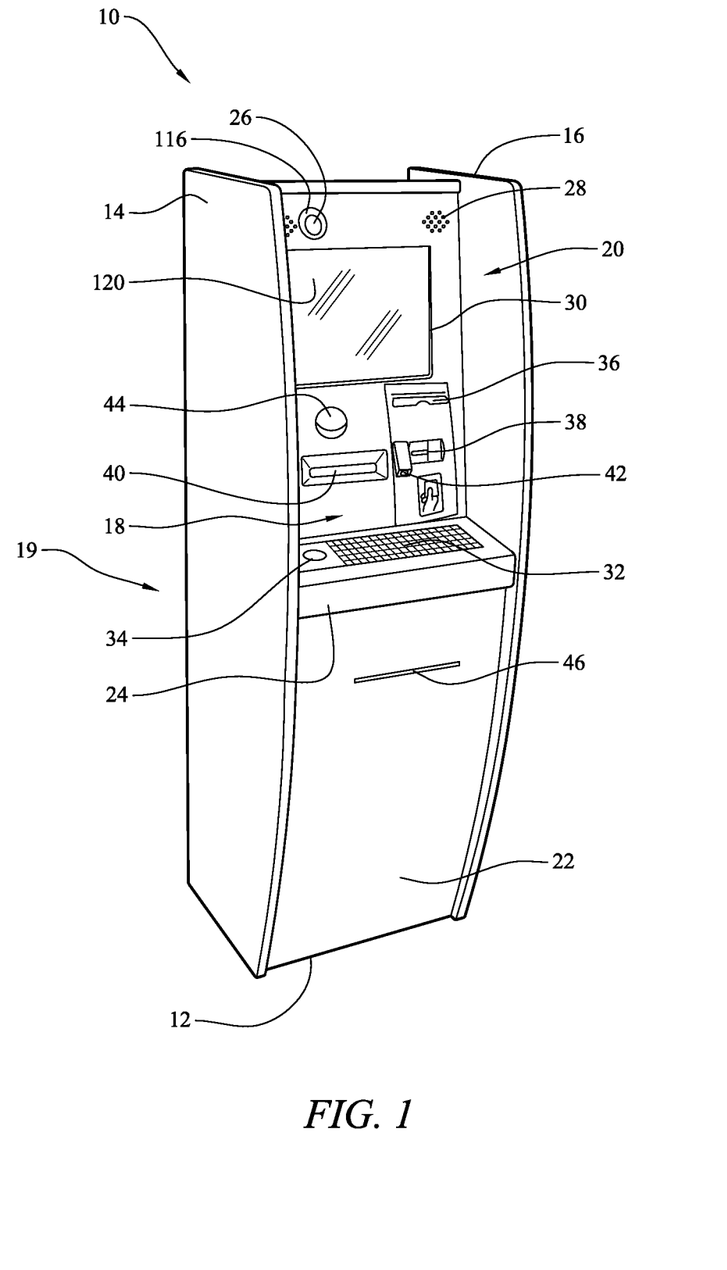
FIG. 1 is a perspective view of an electronic kiosk system, in accordance with the present invention.
Figure 2:
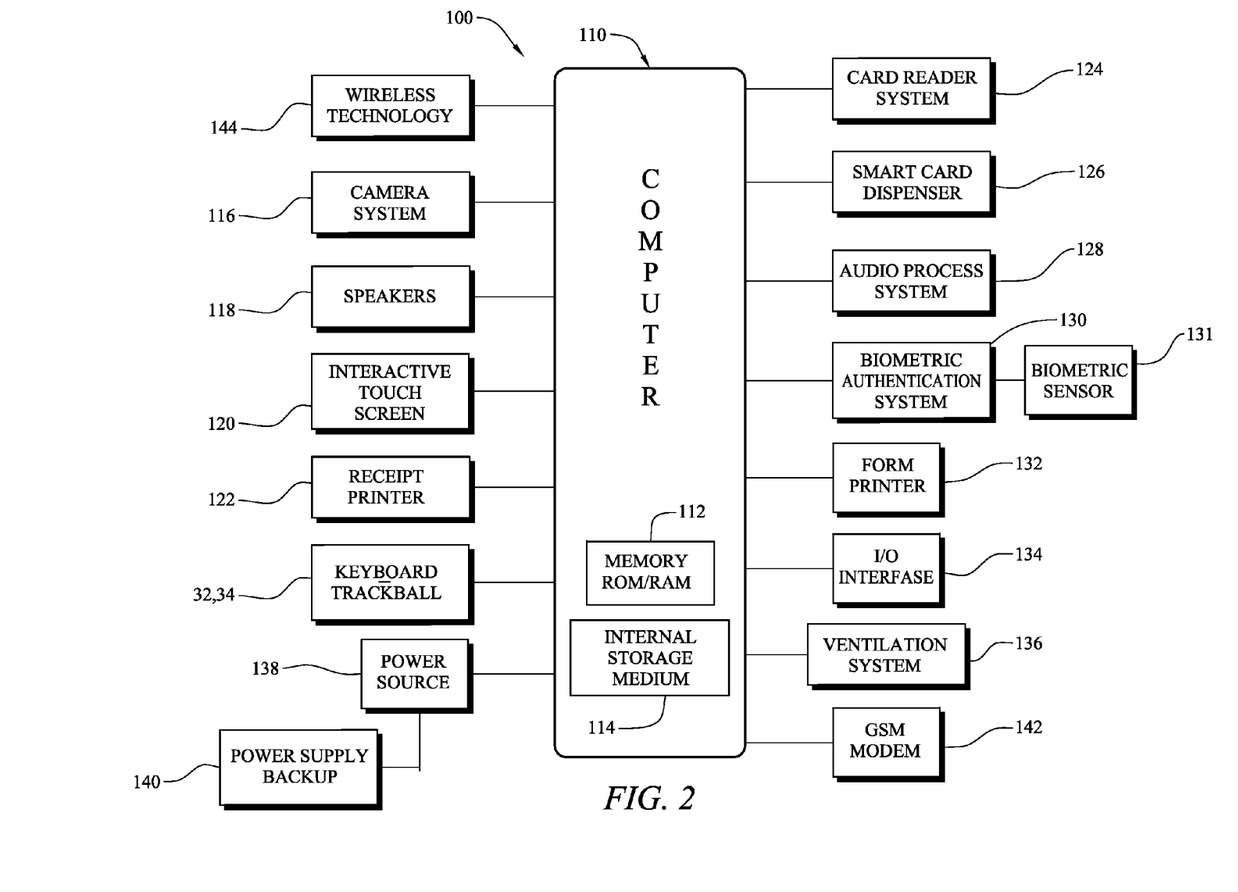
FIG. 2 is a block diagram of the components of the electronic kiosk system of FIG. 1, in accordance with the present invention.

FIGS. 1 and 2 show a perspective view, and a block diagram of components, respectively, of an electronic kiosk system in accordance with one embodiment of the present invention. The structural framework of electronic kiosk 10 includes a base 12, two sidewalls 14, 16 attached to and extending vertically upwards from the base 12, a central panel 18, a front panel 20, and a lateral shelf 24. The central panel 18, front panel 20 and lateral shelf 24 are disposed between sidewalls 14 and 16. As seen in FIG. 1, central panel 18 is setback a distance from the front, longitudinal edges of sidewalls 14, 16 to define a zone of privacy, generally denoted at 20. The zone of privacy 20 provides a level of comfort and security to individuals using the electronic kiosk 10. The structural elements are assembled together to form a chamber for securely housing the operative computer system and components necessary for operating the electronic kiosk 10. A rear panel 19 is attached to the back of the kiosk 10 via, hinges, to provide controlled access to the operative system components of the kiosk 10. Rear panel 19 may include vents to allow heat and air to circulate in and out of the kiosk 10 to help dissipate heat generated by the computer system and operating components. Preferably, rear panel 19 includes a combinational or keyed lock to deter unauthorized personnel from attempting to access the computer operating systems and other components within the interior of kiosk 10. The base 12, sidewalls 14, 16, central panel 18, front panel 20, shelf 24 and rear panel 19 may all be constructed from wood, plastic, metal or any combination thereof. For example, in one non-limiting example, the central panel 18, front panel 22, and rear panel 19 may comprise aluminum or steel, while the vertically extending sidewalls 14, 16, and shelf 24 may comprise wood. The dimensional configuration of the electronic kiosk 10 is selected for allowing young and mature adults to use the operative features of the kiosk 10 with ease and comfort.

Electronic kiosk 10 includes a computer operating system 100 necessary to operate kiosk 10 for dispensing medical smart cards, and managing healthcare information and services. Preferably, computer operating system 100 includes a computer 110 having a processor, read-only memory (ROM) and read-access memory (RAM) 112, and internal storage 114 such as an internal hard drive for storing information, application software, operating programs and the like. The computer 110 is electrically coupled to a number of different operating components or elements as described further below.

A circular camera aperture 26 is formed within a top section of the central panel 18 to expose a high definition (HD) digital camera 116. High definition camera 116 includes or is electrically coupled to a camera processing unit for capturing, processing and recording activity associated with the use of electronic kiosk 10. As with many ATM machines, digital camera 116 also provides a tool for recording suspect activity of persons who are using the electronic kiosk 10. Camera processing unit may include removeable digital storage, a video recorder and processor, or can be designed to take still photographs. The digital storage may include an electronic card, USB flash stick, external hard drive or other well-known storage devices.

With continued reference to FIGS. 1 and 2, central panel 18 includes a plurality of speaker holes 28 formed within the panel 18 and associated with audio speakers 118 provided within kiosk 10. The audio speakers 118 may comprise mono or stereo speakers and are used to provide audible information to user's such as directions, instructions, or other information. The volume of speakers 118 may be adjustable via, hardware or software. For example, a potentiometer may be included within the kiosk to increase or decrease the volume.

A large square-shaped window 30 is formed in the central panel 18 for providing viewing accessibility to an electronic visual display 120 that is securely mounted within kiosk 10. The electronic visual display 120 preferably includes a large, interactive touch screen for allowing users to interface with kiosk 10 by directly touching the screen without the need for using a keyboard 32. Medical management application software is executed, via computer 110, to display icons, tabs, links, and menus on the touch screen for allowing users to interact with the application software when managing medical healthcare information and services. Electronic visual display 120 may include a liquid crystal display (LCD), a cathode ray tube (CRT), a touch screen monitor, or any other suitable display unit. Electronic visual display 120 may include a color or chromatic display, and comprise any type of touch technology including resistive, surface wave, or capacitive.

One alternative method of interacting with kiosk 10 and the electronic visual display 120 is provided by keyboard 32 and trackball 34. The keyboard 32 and trackball 34 are used for inputting or selecting data, and navigating and/or scrolling through data screens, forms, or other information displayed on touch screen 120. Preferably, keyboard 32 comprises a traditional keyboard having standard function keys; however, particular keys associated with designated functions may be included. For example, there may be keys designated to form a particular function. Both the keyboard 32 and trackball 34 are preferably secured within or on the lateral shelf 24. Keyboard 32 may include a water-resistant or water-repellant covering for protecting the keys from damage as a result of the keys being exposed to water or other liquids. This feature may prove to be beneficial where individuals using the electronic kiosk 10 are carrying drinks.

Kiosk 10 includes a central interface area located in the central area of the kiosk 10 for comfortably allowing users to interface with the kiosk 10 when applying for a medical smart card, or managing healthcare information and services. Located in central interface area of kiosk 10 is a receipt printer slot 36 that is operatively associated with a receipt printer 122. The receipt printer 122 is operated by computer 110 to provide hard copies of receipts evidencing payments made using credit cards, charge cards, or banking accounts. The receipt printer 122 may also be adapted to provide information or data relating to various transactions. For example such information may include, but is not limited to, the times and dates when information was processed, the type of accounts or databases a card member accessed, confirmation of prescription refills provided, notifications of system changes or alerts, or other information relating to managing healthcare information or services. The receipt printer 122 may include a color, or black and white ink, and may comprise a dot-matrix printer or laser printer. The receipt printer 122 is easily accessible for maintenance via, the rear panel 19 of kiosk 10.

As seen in FIG. 1, a card reader slot, designated at 38, is also provided in the central panel 18 for receiving medical smart cards, credit cards or charge cards. Card reader slot 38 is operatively associated with a card reader system 124 that includes a contact card reader and a contactless card reader. Computer 110 electrically communicates with the card reader system 124 to control the operation of the card reader system 124 by processing data signals and executing routines, instructions and software programs that are generally stored in memory 112. In one embodiment, card reader system 124 includes a card sensor and necessary electronic components, and circuitry needed for electrically interfacing with contact smart cards and/or credit cards. Such cards generally include electrical contacts (or contact pad) disposed on the card for electrically connecting with electrical contacts located in the card reader system 124. When a contact smart card is inserted within card slot 38, contact card reader 124 communicates with the card and reads the information stored on the card. Computer 110 processes the information and the information and data is sent to display 120 for viewing. Card reader system 124 may also include a magnetic head reader for reading information stored on cards having a magnetic stripe.

Card reader system 124 is also used to interface with credit cards or other charge cards for processing financial payments or transactions. Electronic kiosk 10 is configured to interface with a credit card service provider or credit card clearing house via, network connection that may include cable, telephone, and satellite. For example kiosk 10 can be configured to communicate with a credit card clearing house for processing credit card payments using an internet network. In one alternative embodiment, the electronic kiosk 10 may also include a bill acceptor slot disposed in the kiosk panel 18 and operatively associated with a bill acceptor for accepting currency in paper form. A user may wish to pay for services or a medical smart card by using paper cash including ones, fives, tens or twenty dollar bills.

In one alternative embodiment of the present invention, the card reader system 124 may also include a contactless card reader. The contactless card reader typically includes a transmitting or reception antenna (not shown) for transmitting and receiving data, and reader circuitry, including cryptography module for providing encryption/decryption protocol, coding/decoding circuitry, modulating/demodulating circuitry, and any additional electronic components and circuits for communicating with medical contactless smart cards. Because security of information is a prime concern, communication between the card reader system 124 and contactless smart cards is enhanced through an encoding or encryption process undertaken by an encryption/decryption protocol. In one embodiment, the encryption process of electronic data is performed using a process or algorithm (generally referred to as a cipher) such as Advanced Encryption Standard (AES 256). The Advanced Encryption Standard includes ciphers based on symmetric key algorithms (private key cryptography). Operating software or hardware based instructions, programs or libraries supporting advanced cryptographic algorithms may be implemented to increase security. Thus, the electronic kiosk 10 includes a card reader system 124 for use with contact cards, contactless cards, and credit cards. For added convenience, a contactless smart card reader symbol (not shown) may be located anywhere on the central panel 18 for alerting users that kiosk 10 is compatible for use with contactless cards.

In the preferred embodiment, electronic kiosk 10 includes a smart card dispenser slot 40 aligned with a smart card dispenser 126 for dispensing medical smart cards. Smart card dispenser 126 dispenses contact smart cards, contactless smart cards or both. An individual may access the electronic kiosk 10 to complete an application or registration process in order to receive a medical smart card. The smart card dispenser 126 includes a storage bin for storing a plurality of plastic cards, an ejector for ejecting smart cards out through slot 40, and processing circuitry for processing user information, storing user information on a medical smart card and activating the smart card. The medical smart card can be issued to a subscriber without any medical information provided by the applicant. In one non-limiting embodiment, the storage bin may be configured to hold up to an N amount of medical smart cards therein. For example, the storage bin can be configured to hold up to 500 smart cards. Both the smart card dispenser 126 and storage bin are easily accessible via, rear panel 19 of the kiosk 10 to make necessary repairs or to reload or refill the storage bin with medical smart cards.

To accommodate individuals having certain disabilities, such as blind people, the electronic kiosk 10 includes an audio access port 42 for electrically interfacing ear phones, head phones or the like to an audio process system 128. The audio process system 128 provides audible instructions, explanations, data, and information on how to apply for a medical smart card, how to manage healthcare information using an already existing medical smart card, how to request prescription refills, or provide general information about the medical application program and services offered through the kiosk 10.

Electronic kiosk 10 provides secured access control to information stored on a medical smart card, and in managing healthcare information and services by including biometric authentication. Electronic kiosk 10 includes a biometric authentication system 130 including a biometric sensor 131 and biometric signature reader for capturing biometric fingerprint signatures of authorized users. A biometric sensor aperture 44 is provided on central panel 18 to provide access to the biometric sensor 131. In the preferred embodiment, the biometric sensor 131 comprises a fingerprint sensor; however, other forms of biometric technology may be implemented such as a palm, speech or retinal recognition. A biometric signature database including biometric signatures of authorized users is stored in memory 112 in kiosk 10, on an external server, or in an external database that is electrically coupled to kiosk 10. Authorized biometric signatures are compared to fingerprint signatures captured by the biometric reader and use access to the kiosk 10 is granted if the captured fingerprint signature correctly matches the stored biometric signature of an authorized user.

In one alternative embodiment, camera system 116 may also be used to provide a two-tier authentication level of security. For example, a camera system 116 may be used to capture the image of a user, and compare the captured image with images of authorized users that are stored in an authorized user image database. The increased level of authentication provides enhanced security to information stored on a medical smart card, or to information stored on an application server, or an external database.

With continued reference to FIGS. 1 and 2, electronic kiosk 10 also includes a form printer slot 46 provided within the front panel 22. The form printer slot 46 corresponds to a form printer 132 that is used to print application forms, healthcare directive forms, authorization to treat forms, service agreement forms, immunization forms, HIPPA privacy statements, or other forms, contracts or agreements relating to medical healthcare of a medical smart card holder. Preferably, form printer 132 prints forms having an 8½×11 format though other formats may be implemented. Form printer 132 may include color, or black and white ink, and like the receipt printer 122, is accessible for maintenance or repair via, rear panel 19. Both form printer 132 and receipt printer 122 may include replaceable or refillable toner or ink cartridges. Paper for both printers 122, 132 can be refilled via, rear panel 19.

The application software program of the present invention may alert administration when either or both ink and paper is low or needs replacement.

The application software of the present invention may include maintenance alert programs to notify administrators of possible problems associated with kiosk 10. For example, the maintenance program may alert administrators that the paper is low, that the ink is low, that the smart card storage bin is low, that particular system components have failed, provide temperature readings internal to the kiosk 10, provide notification of suspect activity when using kiosk 10, or that the kiosk 10 is off line.

Also included within the kiosk 10 is an input/output (I/O) interface 134 for electrically interfacing or connecting kiosk 10 to a variety of external devices or networks. The I/O interface 134 may include a telephone modem, routers, a cable modem, universal serial bus (USB) and/or Ethernet ports, parallel or serial connectors, HDMI connections, earphone or microphone jacks, and other electrical connections needed for interfacing with electronic devices. For example, kiosk 10 may be connected to external devices or networks, such as data storage devices, a printer, a keyboard, to a wired network such as the internet, or to other kiosks or card readers. The I/O interface 134 may be situated within kiosk 10, located on the rear panel 19, or disposed anywhere about sidewalls 14, 16.

To help dissipate heat generated from operating system components located within kiosk 10, the kiosk 10 is equipped with a ventilation system 136. The ventilation system 136 may include one or more electric fans controlled by the computer 110 to forcibly circulate air in and out of the kiosk 10. A plurality of vents (not shown) may be formed anywhere within sidewalls 14, 16, rear panel 19, or front panel 22 to direct the circulated air out through the vents. Temperature sensors may be placed within the housing of the kiosk 10 to sense the internal temperature and to activate the ventilation system 136 when the temperature reaches an upper limit. As noted, the application software may be configured to sense internal temperature and alert administration in the event the internal temperature exceeds acceptable limits.

Kiosk 10 is powered, via power supply 138 which includes transformers, AC/DC converters, voltage regulators, rectifiers, fuses, and filters needed to provide clean, stable power to the electronic components, circuits and systems of kiosk 10. In a preferred embodiment, kiosk 10 is configured to connect to a 110 volt AC power supply outlet. The kiosk 10 of the present invention includes the benefit of a backup power supply 138. The backup power supply 140 is used to power kiosk 10 in the event the primary power supply 138 fails or is interrupted as a result of a power failure. The backup power supply 140 may comprise one or more rechargeable or replaceable batteries.

In one embodiment, kiosk 10 includes a computer readable medium having medical management application software and programs stored thereon that when executed on the kiosk 10 displays an interface, on the interactive touch screen 120, comprising a plurality of different menus, information screens, links, icons, tabs, and task bars for managing healthcare information and services of individuals. For example, the medical application software provides a home page menu including user viewable files, documents or information associated with information relating to, the medical management service system, making payments, the application and registration process, help menus for using the kiosk and medical smart card, printing forms, logging into and out of member accounts, scheduling medical appointments, requesting prescription refills, or managing, adding, and editing medical healthcare information.

The computer readable medium may include CD-ROMs, optical disks, floppy diskettes, ROMs, RAMs, EPROMs, EEPROMs, magnetic or optical cards, flash memory, servers, processors or microprocessors with memory, hard drive, or other types of machine-readable mediums suitable for storing electronic instructions, programs or application software. Alternatively, the methods may be performed by a combination of hardware and software.

The application software of the present invention provides an avenue for selecting, amending, viewing, printing, adding, deleting, updating, and scheduling medical information and services. In one embodiment of the present invention, the application software is configured to provide a plurality of menus, icons, links, and tabs that are associated with collecting and managing information, including but not limited to the following:

1. User Demographics: Includes personal profile information of a subscriber such as contact addresses, numbers and information, social security information, insurance information, religious preferences, employer information, vaccine or immunization administration record, and the like;

2. In Case of Emergency Contacts (ICE): Includes information pertaining to individuals that a subscriber wishes medical personnel to contact in the event of an emergency. The ICE information includes names, addresses, telephone numbers, email addresses, or other contact information of primary, secondary and tertiary contact individuals;

3. Physicians and/or Specialists: Includes names, addresses, and contact information of a subscriber's primary care and specialist care physician, the hospital or clinic associated with the physician or specialist, and the like. For example, the name and contact information of a cardiologist, proctologist, or ophthalmologist may be included;

4. Current Medical Conditions: Subscriber related information regarding historical or present medical conditions or diagnosis may be listed herein. For example, information indicating that a subscriber suffers from a particular illness such as diabetes, high blood pressure, or cardiovascular disease may be includes. Also whether the person has a pace maker or an insulin pump, and whether the person suffers from any allergies, requires particular treatment, or is unable to tolerate certain medications, and the like;

5. Information of Historical Procedures: Includes information pertaining to medical procedures a subscriber may have received in the past. The information includes materials associated to medical procedures conducted such as any surgeries, related medical scans, colonoscopy, chemotherapy, and the like;

6. Advance Directives: Provides a list of wishes regarding health care and life-saving techniques often employed by Emergency Medical Technicians, physicians, nurses or other medical personnel during an emergency. The system retains a signed and notarized copy of a subscriber's directives. Evidence of a subscriber's wishes can include, but is not limited to, a Living Will, a power of attorney, a contract agreement, an authorization for emergency medical care, or an authorization to treat. An authorization to treat and a service agreement is subject to HIPPA, the American Recovery and Reinvestment Act (ARRA), and state and local privacy laws. A member may amend or replace any directive by providing a new document. All replacement documents must be signed, notarized and sent to the card administration office. Other documents such as donor information forms may also be included;

7. Prescriptions and Over the Counter (OTC) Medicines: Includes information or data regarding the historical, present or historical and present use of prescription medicine, and over the counter medicine including the amount, brand, dosage, and scheduled times for taking the medicines or prescriptions; and 8. Web Documentary Library: Includes documents and forms such as a Service Agreement, an Authorization to Treat, Advanced Directives, an Authorization for a Dependent Child, a School Immunization Form, a Traveler Profile, a HIPPA Privacy Statement, a Power of Attorney, a Living Will, or any other medical information such as MRI or CT scans, reports, lab or test results or reports, results of blood work, samples taken or provided, and the like.

The fees in providing member services can be predetermined and modified over time. A fee structure is implemented to cover member services that include: providing a medical smart card, managing healthcare information, and requesting prescription refills. In one non-limiting example, an initial fee of $49.95 may be provided with a yearly renewal rate of $29.95. The application software may provide an icon or tab associated with a fee layout or fee plan(s) to inform individuals of applicable fees.

The kiosk 10 includes a secure Global System for Mobile Communication (GSM) connection. A GSM modem 142 is electrically connected to computer 110 to allow the computer 110 to communicate over a mobile network. The GSM modem 142 provides mobile internet connectivity and can be used for sending and receiving SMS and MMS messages.

Figure 3:
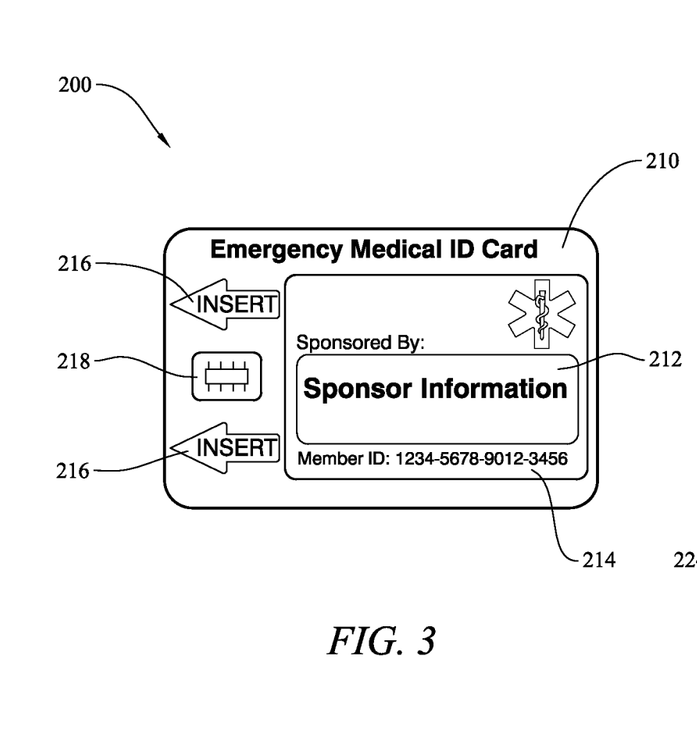
FIG. 3 is a front view of a medical smart card, in accordance with one embodiment of the present invention.
Figure 4:
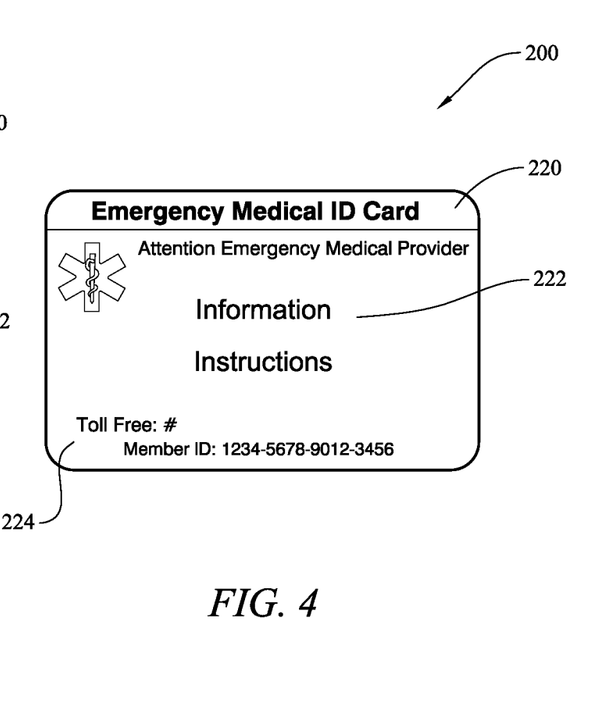
FIG. 4 is a back view of the medical smart card of FIG. 3, in accordance with one embodiment of the present invention; and finally.

The electronic kiosk system of the present invention includes an electronic kiosk 10 accessible to individuals who wish to apply for and receive a medical smart card. The medical smart card can provide vital medical information about the card holder to medical service providers in the event the card holder cannot communicate. One exemplary form of a medical smart card 200 is shown in FIGS. 3 and 4. The term "medical smart card" as used herein refers to any one of a contact card or a contactless card. As a contact card, medical smart card 200 includes a memory chip or integrated circuit that is coupled to electrical contacts or an electrical pad that interfaces with electrical contacts in contact card reader system 124. As a contactless card, smart card 200 includes a smart chip or integrated circuit electrically coupled to an antenna adapted for receiving and/or transmitting data to the card reader system 124.

Medical smart card 200 includes a pocket-sized card fabricated from a plastic material such a polyvinyl chloride. As seen in FIG. 3, the front side 210 of medical smart card 200 includes a central sponsor region 212 dedicated for providing sponsorship information. Sponsor information may include the name or title of a business, facility, department store, pharmacy, or any other business enterprise that promotes or encourages the use of the kiosk 10 for managing healthcare information and services. Contact information relating to the sponsor such as business address, phone numbers or internet website addresses may also be provided adjacent the sponsor identification. For example, a kiosk 10 that is situated at a particular department store would include medical smart cards 200 that include sponsorship information about that particular department store printed in the sponsorship region 212 of the card.

Each medical smart card 200 includes a member identification number 214 printed on the front 210. The member identification number 214 is a number that is uniquely assigned to each person upon completing the registration process. A number of orientation indicators, such as a pair of arrows, designated at 216 are included on the face of the medical smart card 200 for indicating the proper orientation and handling of the medical smart card 200 when using inserting the smart card 200 into the card reader slot 38 of kiosk 10. Card 200 includes a storage device 218 such as a memory chip, integrated chip, smart chip, a microprocessor, or any combination thereof. Card 200 may include an integrated antenna that is electrically coupled to the chip. Storage device 218 is used for storing medical healthcare information.

FIG. 4 shows a back side view of the medical smart card 200. In one non-limiting embodiment, instructions and supplemental information 222 is printed on the back 220 of the smart card 200 to alert emergency medical providers that vital life-saving information of a patient member is stored on the card 200 and that such information is accessible via, a card reader. In the event the medical service provider does not have access to a card reader, member medical information may be obtained by following the instructions printed on the back 220. The instruction may include information directing attending medical personnel to contact member services to acquire patient healthcare information. Further a telephone number 224 may be included to provide contact information in the event medical service provider, who does not have access to a card reader, wishes to access the information stored on the smart card 200. Upon request, the medical healthcare information of a patient can be faxed to a hospital, clinic, or designated location. Other related information may also be printed on the back 220 of the smart card 200 such as email addresses, website addresses, fax numbers, or other contact information or resources. Instructions, directives and alerts may be marked in bold, dark lettering allowing service providers to quickly and easily view the information.

As a security measure, medical smart card 200 may include one or more passwords or PIN numbers embedded within the storage device 218 to increase access security. In addition, a picture of a card holder can be stored on the card. The cardholder's picture can be viewed by authorized personnel to determine the correct identity of the card holder when providing medical care or granting access. The picture stored on the card may also be compared to the picture captured by the camera system 116 to provide security.

The electronic kiosk 10 of the present invention is made accessible to both potential and existing members by placing kiosk 10 in various locations, preferably in high traffic areas. Kiosk 10 may be placed in department stores, pharmacies, shopping centers and malls, in clinics, hospitals, and other medical service provider locations, retail stores, grocery stores, convenient stores, offices, and the like. Banners, indicia, advertising, or logos may be disposed on the outer surface of the kiosk 10.

Individuals will access to a number of kiosks 10 located at various businesses and commercial entities. Generally, a service web home page is displayed on the interactive touch screen 120 of kiosk 10. A potential member can easily navigate through the registration or application process by accessing icons, menus, and tabs that are presented on the interactive touch screen 120. The individual can interact directly with the touch screen 120 to make the appropriate selections, or use the keyboard 32 and trackball 34.

To initially receive a medical smart card 200, an individual must complete an application process and pay applicable fees. To begin the application process, the individual places a finger on the biometric sensor 131 to allow the biometric authentication system 130 to read and process the person's biometric fingerprint signature. The management service provider stores the fingerprint signature in a biometric signature database that is located within kiosk 10 or is accessible over a network connection. In addition, the camera system 116 captures an image of the person and stores the image in an image database. The individual continues to enter personal profile information such as name, contact information such as address, phone numbers and emails. It will be noted that the person is not required to enter all medical healthcare information in the application stage in order to receive a medical smart card. However, the person may continue to enter his or her medical healthcare information, if desired. The medical information may include in case of emergency contacts, information about physicians/specialists, current medical conditions, and procedures, prescriptions and over the counter medicine used, and any other medical information. When all medical information has been provided, the medical information will be verified by the individual's doctor. A message indicating such will be provided when the medical smart card is activated.

Through a web document library, various forms may be obtained via, form printer 132. Examples of such forms include but are not limited to, a Service Agreement, a Privacy Agreement, Health Insurance Portability and Accountability Act release, DNR forms, and any other directives or forms. Through the home menu page of the application software, an individual may select healthcare related forms and print the forms out. The printed forms are forwarded through the form slot 40 and can be completed, properly notarized, and returned to member service provider administrator for proper processing and storage.

After entering the requisite information, the individual may insert a credit card in the card reader system 124 to make payment according to a provided fee schedule. A receipt, evidencing the transaction, is printed, via, receipt printer 122, and a hard copy of the receipt is forwarded through receipt slot 36. Upon payment, the smart card dispenser 126 dispenses a medical smart card 200 through slot 40. The information stored on the medical smart card 200 can be verified and updated on a subsequent visit to a participating physician.

A card member can access kiosk 10 anytime for viewing, editing and printing healthcare information stored on the medical smart card 200. To access healthcare information stored on medical smart card 200, a user simply inserts the medical smart card 200 into the card reader slot 38 and places a finger on the biometric sensor 130. Biometric authentication system 130 processes the fingerprint signature, and compares the fingerprint signature with acceptable fingerprint signatures stored in a biometric signature database. If the biometric fingerprint signature of the card member matches an authorized fingerprint signature stored in the biometric signature database, the card member is granted access to the information stored on the smart card 200. Further, the camera system 116 captures the image of the card member while the card member stands in front of the kiosk 10. The captured image may be compared to a previously stored image and if a match is satisfied, the card member is granted access to the information stored on the medical smart card 200. Thus, in one embodiment, kiosk 10 may provide a two-tier level of authentication to provide secure access control to the information stored on the medical smart card 200.

In one alternative embodiment, the electronic kiosk system of the present invention may require yet another level of authentication. The electronic kiosk 10 may require a medical service provider's access identification number or password to prevent card members from altering critical medical information without the knowledge and consent of a reviewing physician. For example, if vital, critical medical information needs to be amended, added or deleted, kiosk 10 may require another level of authentication be satisfied. In one embodiment, an authorized medical service provider, such as a physician, is required to enter a user ID number that was previously assigned to him or her. The assigned ID number is compared to authorized ID numbers stored in an authorized ID database. If the assigned ID number correctly matches an authorized ID number, the authentication process is satisfied and the physician is granted access to information stored on medical smart card 200 and allowed to make critical changes to a patient's medical record. Physician ID authentication helps prevent members from altering or falsifying medical information.

The electronic kiosk 10 allows members to manage healthcare services such as requesting prescription refills. A member may access a prescription refill menu provided on the home page menu of the kiosk 10. To initiate the process, a member simply inserts the medical smart card 200 in the kiosk 10 via card reader slot 38, and accesses the prescription refill menu. Once activated, the prescription refill menu may present the member with several questions. For example, the member may be asked whether the refill request is for the member or a member's dependent. Further, a list of active prescriptions may also be presented to the member for proper selection. For example, if the member has two current prescriptions still enforceable, a list identifying the brands, dosages and number of refills remaining is presented to the member for selection. Using either the interactive touch screen 120, keyboard 32, or trackball 34, the member makes the proper selection. A confirmation of the member's selection is subsequently provided to the member for review and acceptance.

Authorized personnel at the doctor's office can review the prescription refill request and determine whether the request is viable in light of authorized refills remaining. If so, the prescription request will automatically be sent to a participating pharmacist at the designated pharmacy. A text message or email is sent to a member's device notifying the member that the refill is ready for pick up. During the application process of receiving a smart card, or anytime thereafter, a member may access an electronic kiosk 10 to provide contact information regarding a member's device such as a pager, computer, tablet, or phone. The member simply provides the email addresses or telephone numbers where prescription refill confirmation is to be sent.

Figure 5:
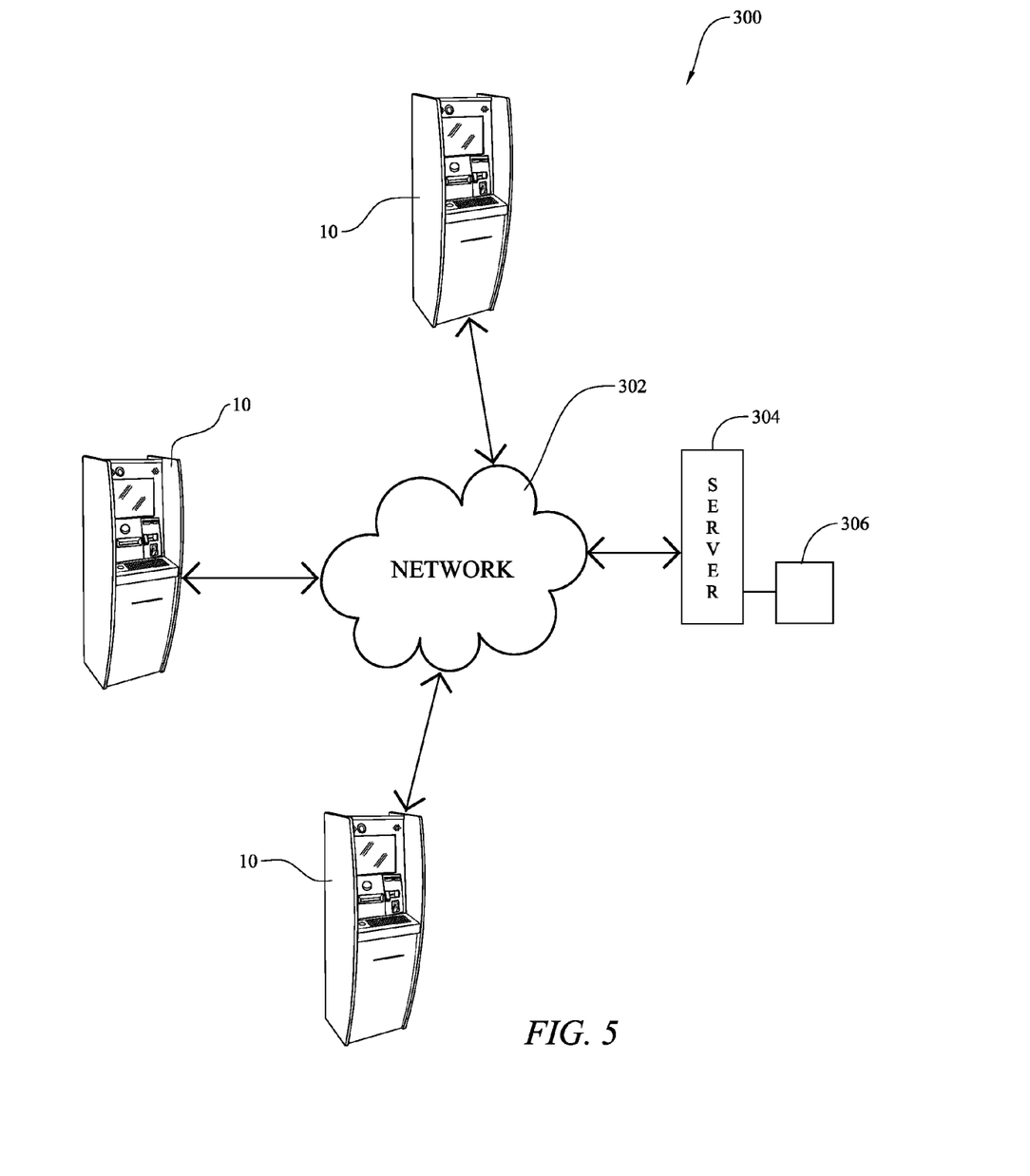
FIG. 5 is a graphical representation of a healthcare management information and service network including a plurality of electronic kiosks of FIG. 1 electrically connected to a server, via a network, in accordance with the present invention.

Turning now to FIG. 5, there is shown a graphical representation of a healthcare management information and service system network 300 including a plurality of electronic kiosks 10 electrically connected to a server 304, via a network 302, in accordance with the present invention. The system network 300 allows a plurality of kiosks 10 to be operated in a client-server configuration to provide medical service providers and existing members' access to medical information, databases, libraries, or web pages provided from a web-based server, or to permit new members to apply for and receive a medical smart card 200. Any conventional web browser can be used with kiosk 10 to display and manipulate data on web pages. The network system 300 allows a plurality of kiosks 10 to be centrally administered by one or more application servers 304. The central management allows controlled application of software updates. Application software is tailored to include a plurality of drop down menus, function specific icons, taskbars, tabs, and user accessible and viewable interlinked HTML or XML files or documents. Conventional website design techniques may be used to create an on-line medical web application software program.

One or more application servers 304 include the requisite memory and processors to store and operate medical application software programs, instructions, computer code, and other processing features. The server 304 may include one or more internal databases, or be electrically coupled to one or more external databases 306. Each electronic kiosk 10 has access to the application server 304, via, a wired or wireless network 302. Each electronic kiosk 10 may include any type of wireless transmission technology 144, including, but not limited to, Wi-Fi, 2G, 3G, 4G, 5G, Blue Tooth or Wi Max. Possible communication networks that may comprise a network or be otherwise part of the system, includes but is not limited to internet, intranet, a local area network (LAN) or a wide area network (WAN), a telephone line, cable, or a satellite communication link. Thus, the applicable medical application software, programs, algorithms, and databases may be loaded on a computer readable medium that resides within each kiosk 10, or alternatively, the medical application software may reside on an application server 302 that is accessible by a plurality of kiosks 10 over a wired or wireless network 302. The client-server configuration permits a number of kiosks 10 to be placed in a variety of different locations where each kiosk connects to an application server 304 over an internet connection. Each kiosk 10 may include a GSM modem 142 to communicate over a mobile network.

It will be understood that although the present invention illustrates an electronic kiosk 10 in the form of a floor kiosk, the present invention is easily and also adapted for use with a variety of different kiosks including mobile kiosks, table kiosks, wall kiosks and portable kiosks.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What we claim is:

1. A card dispensing kiosk comprising:
   a frame including a base joined to two vertical sidewalls extending upwards from
   said base, a central panel, a front panel, a rear panel, and a lateral shelf, all assembled together to form a chamber for housing a computer system for operating electronic components including:
   an interactive touch screen accessible through an opening formed in said central panel;
   a first printer for printing receipts, and a second printer for printing healthcare related forms, said first printer associated with a printer slot provided in said central panel, and said second printer associated with a second printer slot provided in said front panel;
   a card reader system selectively interfacing with medical smart cards including
   healthcare information stored on said medical smart card, and credit cards;
   a card dispenser associated with a card dispensing slot provided in said central panel, said card dispenser sequentially dispensing said medical smart cards upon each successful completion of an application process;
   a biometric authentication system including a biometric sensor situated on said central panel;
   a high definition camera operated to capture images of individuals using said kiosk; and
   a keyboard disposed on or within said lateral shelf, wherein said central panel is setback a distance from front longitudinal edges of said vertical sidewalls to provide a zone of privacy; wherein
   said healthcare information includes an individual's demographic and profile information, medical emergency contact information, physician/specialist information, medical conditions, procedural medical history, information relating to prescription and over-the-counter medicine, vitamins or supplements, vaccination or immunization historical records, advance directives, medical insurance information, and a photograph of an individual owner of said medical smart card, and wherein said healthcare related forms includes any of service agreements, authorizations to treat, advanced directives, immunization forms, privacy statements, laws and rules, power of attorney, and living will.

2. The card dispensing kiosk of claim 1, wherein said computer system includes a processor, memory, an internal hard drive, and software including medical application software and programs.

3. The card dispensing kiosk of claim 2, further including an audio system electrically coupled to said computer system and including one or more speakers associated with speaker holes formed in said central panel, and a trackball located adjacent said keyboard.

4. The card dispensing kiosk of claim 3, further including a ventilation system for circulating air out from and within said chamber.

5. The card dispensing kiosk of claim 4, further including wireless technology including any one of 2G, 3G, 4G, 5G, Wi-Fi, WiMax or Blue Tooth technology, a secure Global System for Mobile Communication (GSM) connection, and a GSM modem.

6. The card dispensing kiosk of claim 5, further including a handicapped audio access port provided on said central panel, said audio access port electrically coupled to said computer system for providing audible information.

7. The card dispensing kiosk of claim 6, wherein said card dispenser includes a card ejector for ejecting smart cards, and a card storage bin for storing a plurality of smart cards therein.

8. The card dispensing kiosk of claim 7, further including an input/output (I/O) interface including telephone or cable connections, modem connectors, universal serial bus (USB) and/or Ethernet ports, parallel or serial connectors, and HDMI connections.

9. The card dispensing kiosk of claim 7, wherein said biometric sensor includes any one of a fingerprint sensor, a palm sensor, a speech recognition system, or a retinal validation sensor, and wherein said biometric authentication system further includes a biometric signature database including biometric signatures associated with a plurality of individuals authorized to use said card dispensing kiosk.

10. A method of managing healthcare information and services comprising:
providing an electronic kiosk comprising:
a frame including a base joined to two vertical sidewalls extending upwards from said base, a central panel, a front panel, a rear panel, and a lateral shelf, all assembled together to form a chamber for housing a computer system including a processor, and memory, and kiosk system components, said computer system electrically connected to and operating said kiosk system components including:
an interactive touch screen;
a first printer for printing receipts, and a second printer for printing healthcare related forms, said printers associated with slots provided in a central panel;
a card reader system selectively interfacing with medical smart cards including healthcare information stored thereon, and credit cards;
a card dispenser associated with a card dispensing slot provided in said central panel, said card dispenser dispensing smart cards;

a biometric authentication system including a biometric sensor situated on said central panel;
a high definition camera operated to capture images of individuals using said card dispensing kiosk;
an audio system including speakers and a handicapped audio access port; and operating an application server hosting medical service application software associated with managing individual healthcare information and services, said electronic kiosk electrically communicating with said application server over a wired or wireless network;
capturing an image with said high definition camera of an individual using said kiosk, and processing a biometric signature of an individual user; and receiving information from an individual user applying for a medical smart card, and sequentially dispensing a medical smart card upon successful completion of each application process completed by individual users, or selectively interfacing a medical smart card with said card reader system of said kiosk to view and manage healthcare information and services when said biometric signature of said individual user is authenticated, said medical smart card including healthcare information;
further including the step of requesting prescription refills of medication, and sending a text or email message confirming readiness of said refills;
wherein the step of processing a biometric signature of an individual user includes the step of reading a biometric fingerprint signature of said user when said user places a finger on said biometric sensor;
wherein the step of providing information of an individual user to apply for a medical smart card includes the step of entering personal information, and paying a fee with a credit card to complete said application process.

11. The method of claim 10, further including the step of printing a receipt via, said first printer, and further including the step of printing said healthcare related forms via, said second printer, said receipt and said healthcare related forms forwarded through a corresponding slot.

12. The method of claim 10, wherein said medical service application software provides an interface on said touch screen including menus, links, tabs and icons for managing healthcare associated with individual users, said medical service application software being executed on said electronic kiosk.

13. The method of claim 12, wherein said healthcare information includes, but is not limited to, demographic and profile information, emergency contact information, physician/specialist information, current medical conditions, medical history, prescriptions, over-the-counter medicines, and supplements, vaccinations or immunization history, advance directives, insurance information, medical test results, labs, or scans, and a picture of a person providing said healthcare information.

14. An electronic kiosk for dispensing and interfacing with medical smart cards, said electronic kiosk comprising:
a computer system having memory and a processor and including:
an interactive touch screen;
a first printer for printing receipts, and a second printer for printing healthcare related forms;
a card reader system selectively interfacing with medical smart cards including healthcare information stored on said medical smart card, and credit cards;
a card dispenser sequentially dispensing medical smart cards upon each successful completion of an application process;

a biometric authentication system including a biometric fingerprint sensor;

a high definition camera operated to capture images of individuals using said card kiosk;

input devices for inputting data; and a machine readable medium including a medical service application software stored thereon that when executed on said computer system displays an interface on said interactive touch screen, said interface comprising menus, links, tabs, and icons, associated with managing said healthcare information, and allowing a user to selectively read healthcare information stored on said medical smart card or to selectively write said healthcare information to said medical smart card when said medical smart card electrically communicates with said card reader system and when said biometric authenticating system correctly authenticates a fingerprint signature of an authorized user; wherein said healthcare information includes an individual's demographic and profile information, medical emergency contact information, physician/specialist information, medical conditions, procedural medical history, information relating to prescription and over-the-counter medicine, vitamins or supplements, vaccination or immunization historical records, advance directives, medical insurance information, and a photograph of an individual owner of said medical smart card, and wherein said healthcare related forms includes any of service agreements, authorizations to treat, advanced directives, immunization forms, privacy statements, laws and rules, power of attorney, and living will.

15. The electronic kiosk of claim 14, further including an audio system including speakers and a handicapped audio access port, and wherein said input devices include a keyboard and a trackball.

16. The electronic kiosk of claim 15, further including a ventilation system, and a backup power supply, aid card dispenser including a storage bin for storing a plurality of smart cards therein.

* * * * *